United States Patent [19]

Sessler et al.

[11] Patent Number: 5,302,714
[45] Date of Patent: Apr. 12, 1994

[54] SAPPHYRINS, DERIVATIVES AND SYNTHESES

[75] Inventors: Jonathan L. Sessler; Michael J. Cyr, both of Austin, Tex.

[73] Assignee: Board of Regents, The University of Texas System, Austin, Tex.

[21] Appl. No.: 966,317

[22] Filed: Oct. 26, 1992

Related U.S. Application Data

[62] Division of Ser. No. 454,298, Dec. 21, 1989, Pat. No. 5,159,065.

[51] Int. Cl.$^5$ ............................................ C07D 245/02
[52] U.S. Cl. ................................... 540/472; 534/560; 540/496; 548/518
[58] Field of Search ............... 540/469, 472; 534/560; 548/518

[56] References Cited

U.S. PATENT DOCUMENTS

| | | | |
|---|---|---|---|
| 4,883,790 | 11/1989 | Levy et al. | 540/145 |
| 4,915,683 | 4/1990 | Sieber | 604/4 |
| 4,935,498 | 6/1990 | Sessler et al. | 534/15 |
| 5,041,078 | 8/1991 | Matthews et al. | 604/4 |
| 5,120,411 | 6/1992 | Sessler et al. | 204/157.15 |
| 5,159,065 | 10/1992 | Sessler et al. | 534/15 |

FOREIGN PATENT DOCUMENTS

| | | |
|---|---|---|
| 0111418A2 | 6/1984 | European Pat. Off. . |
| 0196515A1 | 10/1986 | European Pat. Off. . |
| 0233701A2 | 8/1987 | European Pat. Off. . |

OTHER PUBLICATIONS

Grigg et al., J. Chem. Soc. (C), 1966, pp. 976-981.
Franck et al., Just Us Liebigs Ann. Chem. 1980 253-274.
Collman et al. JACS 1981 103 516-533.
Tindall, Ind and Eng. Chem. 33(1), 1941 65-66.
Kambe, et al., Bull. Chem. Soc. Japan 41(6) 1444-1446, 1968.
Harriman et al., "Metallotexaphyrins: A New Family of Photosensitisers for Efficient Generation of Singlet Oxygen," *J. Chem. Soc., Chem. Commun.*, 314-316, 1989, published in Europe.
Sessler et al., "A Water-Stable Gadolinium(III) Complex Derived from a New Pentadentate Expanded Porphyrin Ligand," *Chem. Absts.*, 111:125716e, Oct. 2, 1989, published in USA.
Sessler et al., "An Expanded Porphyrin: The Synthsis and Structure of a New Aromatic Pentadentate Ligand," *J. Amer. Chem. Soc.*, 110(16):5586–5588, 1988, published in USA.
Cueller, Edward A. et al., "Synthesis and Characterization of Metallo and Metal-Free Octaalkylphthalocyanines and Uranyl Decaalkylsuperphthalocyanines," *Inorg. Chem.*, 20:3766–3700, 1981, published in USA.
Bauer, Victor J. et al., "Sapphyrins: Novel Aromatic Pentapyrrolic Macrocycles," *J. Am. Chem. Soc.*, 105:6429–6436, 1983, published in USA.
Rexhausen, Hans et al., "The Synthesis of a New 22 $\pi$-Electron Macrocycle: Pentaphyrin," *Chem. Soc., Chem. Commun.*, 1983, published in Europe.

(List continued on next page.)

*Primary Examiner*—Mukund J. Shah
*Assistant Examiner*—Y. N. Gupta
*Attorney, Agent, or Firm*—Arnold, White & Durkee

[57] ABSTRACT

The present invention involves, in addition to many unique substituted sapphyrins, a novel method for synthesizing sapphyrins with good efficiency and high yield. An improved 9-step synthesis of substituted sapphyrins, e.g., the two C$_2$ symmetric sapphyrins, compounds 2 and 4 of FIG. 1C, is described herein. This synthesis involves as an important step the condensation between a tripyrrane diacid and a diformyl bipyrrole. The key tripyrrane component is prepared in three high-yield steps from readily available pyrrolic precursors and the bipyrrole portion is prepared in four steps from ethyl 3-methyl-4-methylpyrrole-2-carboxylate in roughly 33% yield overall.

10 Claims, 5 Drawing Sheets

OTHER PUBLICATIONS

Broadhurst, M. J. et al., "18- and 22-π-Electron Macrocycles Containing Furan, Pyrrole, and Thiophen Rings," *Chem. Commun.*, 1480–1482, 1969, published in Europe.

Broadhurst, M. J. et al., "The Synthesis of 22 π-Electron Macrocycles. Sapphyrins and Related Compounds," *J. Chem. Soc.*, Perkin I, p. 2111, 1972, published in Europe.

Marks, Tobin J. et al., "Large Metal Ion-Centered Template Reactions. Chemical and Spectral Studies of the Superphthalocyanine Dioxocyclipnetakis (1-iminoisoindolinato) Uranium(VI) and Its Derivatives," *J. Am. Chem. Soc.*, 1978, pp. 1695–1705, published in USA.

Sessler et al., "Synthetic and Structural Studies of Sapphyrin, a 22-pielectron Pentapyrrolic 'Expanded Porphyrin'," *J. Am. Chem. Soc.*, 112:2810–2813, 1990, published in USA.

Broadhurst and Grigg, "New Macrocyclic Aromatic Systems Related to Porphins," *Chem. Commun.*, pp. 23–24, 1969, published in Europe.

Gossauer, "Syntheses of Some Unusual Polypyrrole Macrocycles," *Bull. Soc. Chim. Belg.*, 92(9):793–809, 1983, published in Europe.

Broadhurst and Grigg, "Preparation of Some Sulphur-containing Polypyrrolic Macrocyles. Sulphur Extrusion from a meso-Thiaphlorin," *Chem. Commun.*, pp. 807–809, 1970, published in Europe.

Sessler et al., "Synthesis and Crystal Structure of a Novel Tripyrrane-Containing Porphyrinogen-like Macrocycle," *J. Org. Chem.*, 52:4394–4397, 1987, published in USA.

Barton and Zard, "A New Synthesis of Pyrroles from Nitroalkenes," *J. Chem. Soc., Chem. Commun.*, pp. 1098–1100, 1985, published in Europe.

Maiya et al., "*In Vitro* Photodynamic Activity of Diprotonated Sapphyrin: a 22-pi-electron Pentapyrrolic Porphyrin-like Macrocycle," *Chem. Absts.*, 112:348–349, Abstract #194584t, 1990, published in USA.

SAPPHYRINS, DERIVATIVES AND SYNTHESES

This invention was made in part with government support under the National Science Foundation Presidential Young Investigator Award (1986) to J. L. Sessler, grant CHE-8552768. The government has certain rights in the invention.

This is a divisional of copending application Ser. No. 07/454,298 filed Dec. 21, 1989, issued as U.S. Pat. No. 5,159,065 on Oct. 27, 1992.

This application is related to other applications filed on an even date herewith. These other applications have at least one inventor and one assignee in common and are are entitled: PHOTODYNAMIC ACTIVITY OF SAPPHYRINS (by Sessler, Maiya and Harriman and PHOTODYNAMIC VIRAL DEACTIVATION WITH SAPPHYRINS (by Sessler, Harriman, Maiya, Judy, Matthews, Newman and Bernal). These related applications are incorporated by reference herein.

BACKGROUND OF THE INVENTION

The present application concerns substituted sapphyrins and sapphyrin derivatives. Sapphyrin, first discovered serendipitously by Woodward, ((a) First reported by R. B. Woodward at the Aromaticity Conference, Sheffield, U. K. 1966; (b) Bauer, V. J.; Clive, D. R.; Dolphin D.; Paine, J. B. III; Harris, F. L.; King, M. M.; Loder, J.; Wang, S.-W. C.; Woodward, R. B. *J. Am. Chem. Soc.* 1983, 105, 6429-6436) is one of the more intriguing products to emerge from initial studies directed towards the synthesis of Vitamin $B_{12}$. (Bauer et al., *J. Am. Chem. Soc.*, 1983; Broadhurst, M. J.; Grigg, R.; Johnson, A. W. *J. Chem. Soc. Perkin Trans.* 1, 1972, 2111-2116; Grigg, R. in *The Porphyrins*, Dolphin, D., Ed.; Academic Press: New York; 1978, Vol. II, pp. 327-391.) It is a 22 pi-electron pentapyrrolic macrocycle that forms a dark blue solid (hence the name sapphyrin) which exhibits an intense Soret-like band at about 450 nm ($CHCl_3$) along with weaker Q-type transitions in the 620 to 690 nm region. These optical properties along with the presence of a large central cavity, which could possibly serve for metal binding, suggest that sapphyrin and its derivatives should be useful for many technologies, including a variety of emerging biomedical applications, notably photodynamic therapy (PDT) (For overviews of PDT see: (a) Gomer, C. J. *Photochem. Photobiol.* 1987, 46, 561-562 (special issue on this topic); (b) Dahlman, A.; Wile, A. G.; Burns, R. G.; Mason, G. R.; Johnson, F. M.; Berns, M. W. *Cancer Res.* 1983, 43, 430-434; (c) Dougherty, T. J. in *Methods in Porphyrin Photosensitization*, Kessel, D., Ed.; Plenum press: New York, 1985; pp. 313-328; (d) Dougherty, T. J. *Photochem. Photobiol.* 1987, 45, 879-889; (e) Gomer, C. J. *Semin. Hematol.* 1989, 26, 27-34; (f) Manyak, M. J.; Russo, A.; Smith, T. D. and Glatstein, E. *J. Clin. Oncol.* 1988, 6 p. 380-391) where long wavelength ($\geq 680$ nm) absorptions are desired, (For a specific discussion of the desirability of obtaining long-wavelength photosensitizers see: Kreimer-Birnbaum, M. *Seminars in Hematology* 1989, 26, 157-173) and magnetic resonance imaging enhancement (MRI) where chelation of highly paramagnetic metal cations such as gadolinium(III) would be particularly worthwhile. (For an introductory discussion of MRI contrast agents see: Tweedle, M. F.; Brittain, H. G.: Eckelman, W. C.; et al. in *Magnetic Resonance Imaging*, 2nd ed., Partain, C. L.; et al. Eds.; W. B. Saunders: Philadelphia; 1988, Vol I., pp. 793-809. For a comprehensive review of paramagnetic MRI contrast agents see: Lauffer, R. B. *Chem. Rev.* 1987, 87, 901-927). However, in spite of being known for over 20 years, almost no work has been devoted to the systematic study of this intriguing "expanded porphyrin", (Grigg, R. in The Porphyrins, Dolphin, D., Ed.; Academic Pres: New York; 1978, Vol. II, pp. 327-391.) in part, perhaps, because of the tedious nature of the synthesis involved. For instance, to date, no well-characterized sapphyrin-based pentacoordinated metal complexes have been reported, although attempts to prepare these materials have been recorded. (Bauer, V. J.; Clive, D. R.; Dolphin, D.; Paine, J. B. III; Harris, F. L.; King, M. M.; Loder, J.; Wang, S.-W. C.; Woodward, R. B. *J. Am. Chem. Soc.* 1983, 105, 6429-6436). In fact, only tetracoordinated metal complexes have been prepared to date from these potentially pentadentate ligand systems. Moreover, in marked contrast to the far better studied 18 pi-electron porphyrins no structural information currently exists for this curious ring system in either its free-base or metalated forms. The present invention comprises an improved synthesis of sapphyrins, as well as the first crystallographic characterization of a sapphyrin.

The original sapphyrin synthesis (Bauer, V. J.; Clive, D. R.; Dolphin, D.; Paine, J. B. III; Harris, F. L.; King, M. M.; Loder, J.; Wang, S.-W. C.; Woodward, R. B. *J. Am. Chem. Soc.* 1983, 105, 6429-6436) (Broadhurst, M. J.; Grigg, R.; Johnson, A. W. *J. Chem. Soc. Perkin Trans.* 1, 1972, 211-2116.) involved MacDonald type [3+2] condensations between a functionalized bipyrrole, analogous to 5, and a dicarboxyl substituted tripyrrane, similar to 6, as shown in FIG. 1C. Both, therefore, suffered from the same drawback, namely that the syntheses of these key bipyrrolic and tripyrrolic precursors were long and tedious.

SUMMARY OF THE INVENTION

The present invention involves, in addition to many unique substituted sapphyrins, a novel method for synthesizing sapphyrins with good efficiency and high yield. In one aspect, this method may be described as comprising the following steps:

(a) reacting an alkyl derivative$_a$ aldehyde and an n-nitromethylenealkyl derivative$_b$ to produce beta-hydroxynitroalkyl derivative$_c$;

(b) reacting the beta-hydroxynitroalkyl derivative$_c$ with acetic anhydride to form beta-acetoxynitroalkyl derivative$_c$;

(c) reacting the beta-acetoxynitroalkyl derivative$_c$ with ethyl isocyanoacetate in the presence of a nonnucleophilic base such as 1,8-diazabicyclo[5.4.0]undec-7-ene, for example, to form ethyl 3-alkyl derivative$_a$-4-alkyl derivative$_b$pyrrole-2-carboxylate;

(d) reacting ethyl 3-alkyl derivative$_a$-4-alkyl derivative$_b$pyrrole-2-carboxylate with iodine and iodide to form ethyl 3-alkyl derivative$_a$-4-alkyl derivative$_b$-5-iodopyrrole-2-carboxylate;

(e) coupling two molecular equivalents of ethyl 3-alkyl derivative$_a$-4-alkyl derivative$_b$-5-iodopyrrole-2-carboxylate in the presence of copper bronze to produce diethyl 4,4'-dialkyl derivative$_a$-3,3'-dialkyl derivative$_b$-2,2'-bipyrrole-5,5'-dicarboxylate;

(f) converting diethyl 4,4'-dialkyl derivative$_a$-3,3'-dialkyl derivative$_b$-2,2'-bipyrrole-5,5'-dicarboxylate to 4,4'-dialkyl derivative$_a$-3,3'-dialkyl derivative$_b$-2,2'-bipyrrole by saponification and decarboxylation;

(g) reacting 4,4'-dialkyl derivative$_a$-3,3'-dialkyl derivative$_b$-2,2'-bipyrrole with dimethylformamide and phosphorus oxychloride to form 3,3'-dialkyl derivative$_b$-4,4'-dialkyl derivative$_a$-5,5'-diformyl-2,2'-bipyrrole;

(h) reacting benzyl 4-alkyl derivative$_d$-3,5-dimethylpyrrole-2-carboxylate with an oxidizing agent such as lead tetraacetate to produce benzyl 5-(X-methyl)-4-alkyl derivative$_d$-3-methylpyrrole-2-carboxylate where X represents a substituent which may leave as an anionically stable leaving group such as acetate anion, iodide, tosylate or bromide;

(i) condensing two molecular equivalents of benzyl 5-(x-methyl)-4-alkyl derivative$_d$-3-methylpyrrole-2-carboxylate with 3-alkyl derivative$_e$-4-alkyl derivative$_f$pyrrole under acidic conditions to produce 2,5-bis(5-benzyloxycarbonyl-3-alkyl derivative$_d$-4-methylpyrrol-2-ylmethyl)-3-alkyl derivative$_e$-4-alkyl derivative$_f$pyrrole;

(j) hydrogenating 2,5-bis(5-benzyloxycarbonyl-3-alkyl derivative$_d$-4-methylpyrrol-2-ylmethyl)-3-alkyl derivative$_e$-4-alkyl derivative$_f$pyrrole to produce 2,5-bis(5-carboxy-3-alkyl derivative$_d$-4-methylpyrrol-2-ylmethyl)-3-alkyl derivative$_e$-4-alkyl derivative$_f$pyrrole; and (k) reacting 3,3'-dialkyl derivative$_b$-4,4'-dialkyl derivative$_a$-5,5'-diformyl-2,2'-bipyrrole and 2,5-bis(5-carboxy-3-alkyl derivative$_d$-4-methylpyrrol-2-ylmethyl)-3-alkyl derivative$_e$-4-alkyl derivative$_f$pyrrole to produce 2,23-dialkyl derivative$_b$-3,22-dialkyl derivative$_a$-7,18-dimethyl-8,17-dialkyl derivative$_d$-12-alkyl derivative$_e$-13-alkyl derivative$_f$sapphyrin.

Figure 3:
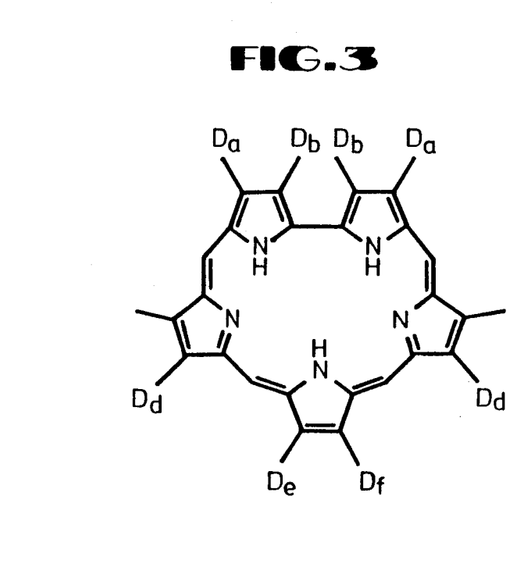
FIG. 3 schematically describes the general sapphyrins synthesized according to the present invention.

The alkyl derivative$_a$, alkyl derivative$_b$, alkyl derivative$_c$, alkyl derivative$_d$, alkyl derivative$_e$ and alkyl derivative$_f$ are independently alkane, functionalized alkane, derivatized alkane or derivatized functional alkane. Functionalized alkanes are considered to include alkanes with one or more chemically reactive substituents such as an amino, hydroxyl, carboxyl, oxide, carbonyl, cyanate, isocyanate, thiocyanate, sulfhydryl, nitrile, diazo, iodine, disulfide, sulfonic or similar groups having chemical or potential chemical reactivity. Derivatized alkanes are considered to include alkanes bound to relatively nonreactive substituents such as aryl, alkenyl, alkynyl, cycloalkyl and the like. Derivatized functional alkanes are considered to include substituents such as amides, esters, ethers, and disulfides. Many other variants are possible and known to those of skill in the chemical arts. This synthetic scheme is outlined in FIG. 5, in analogy to the more specific scheme of FIG. 1A–1C. FIG. 3 schematically designates the product of the more general synthetic scheme of FIG. 5.

An improved 9-step synthesis of substituted sapphyrins, e.g., the two $C_2$ symmetric sapphyrins, compounds 2 and 4 of FIG. 1C, is described herein. This synthesis involves as an important step the condensation between a tripyrrane diacid and a diformyl bipyrrole in analogy to the earlier work of Woodward (Bauer, V. J.; Clive, D. R.; Dolphin, D.; Paine, J. B. III; Harris, F. L.; King M. M.; Loder, J.; Wang, S.-W. C.; Woodward, R. B. *J. Am. Chem. Soc.* 1983, 105, 6429.) and Johnson (Broadhurst, M. J.; Grigg, R.; Johnson, A. W. *J. Chem. Soc. Perkin Trans.* 1, 1972, 2111.). It differs from these earlier syntheses, however, in the efficient manner in which these key precursors are prepared. In the present approach, the key tripyrrane component is prepared in three high-yield steps from readily available pyrrolic precursors and the bipyrrole portion is prepared in four steps from ethyl 3-ethyl-4-methylpyrrole-2-carboxylate in roughly 33% yield overall. Single crystals of the diprotonated form of the decaalkyl sapphyrin 2 were obtained by forming the dichloride salt (by washing a $CH_2Cl_2$ solution of compound 2 with aqueous HCl), exchanging the chloride counter ions with $AgPF_6$, and subjecting to diethyl ether vapor diffusion. The crystals so obtained were characterized by structural and chemical means as the mono hexafluorophosphate fluoride salt of the diprotonated sapphyrin 2([2(2H+)F−][PF$_6$−]) with the key fluoride counter ion being centrally bound within the fully protonated pentaaza core. As such, the fully protonated sapphyrin 2 is a new example of an anion receptor. The material crystallizes in space group $C_{2h}^5$–$P2_1/c$ of the monclinic system with 4 formula units in a cell of dimensions a=9.148(1), b=26.880(2), c=15.229(1) Angstrom, beta=92.87(1)°. The structure has been refined to values of $R(F^2)$ of 0.093 and $R(F)$ (for $F^2>3\text{sigma-}(F^2)$) of 0.065 for 7867 observations and 682 variables. The F resides centrally within the core with N—H···F distances of 2.697(3) to 2.788(3) Angstrom and angles of 167(2)° to 177(3)°. Such a specific affinity could lead to development of an electrode and/or sensor useful to measure the presence of ions such as fluoride.

Certain decaalkyl sapphyrins of the present invention have been found readily soluble in chloroform and/or methanol which distinguishes them from those previously produced. This solubility confers a potentially great advantage for many purposes, including photodynamic tumor therapy and viral deactivation. Additionally, these compounds should be useful in production of materials such as laser-read compact disks for sound or other recordings.

The mono or dicarboxy sapphyrins or dioxosapphyrins of the present invention are soluble in aqueous media, which should facilitate biological and medical uses. Such carboxy compounds, as well as other possible functional substituents also lend themselves to coupling to solid matrices, as well as to biological molecules such as antibodies. Coupling to solid matrices could be combined with photodynamic viral deactivation processes. For example, viral-contaminated blood could be passed through a column of sapphyrin-matrix beads under sufficient illumination to generate singlet oxygen or otherwise deactivate viruses without adding soluble sapphyrin to the blood.

The sapphyrins of the present invention may also be readily prepared in quantities adequate for the above uses.

It is believed that pentavalently coordinated lanthanide$^{3+}$ metal (e.g., Gd), In, Y and actinide cations complexes should be obtainable from the sapphyrins of the present invention, as well as the dioxosapphyrins thus produced. Such lanthanide metal complexes should prove useful in medical imaging processes, including magnetic resonance imaging.

Described herein is the specific preparation of a new decaalkyl derivative 4,9,13,14,18,23-hexaethyl-3,8,19,24-tetramethyl-25,26,27,28,29-pentaazahexacyclo[20.2.1.1$^{2,5}$.1$^{7,10}$.1$^{12,15}$.1$^{17,20}$]nonacosa-2,4,6,8,10(28),11,13,15,17(26),18,20,22,24-tridecaene or 3,8,12,13,17,22-hexaethyl-2,7,18,23-tetramethylsapphyrin and a new and unprecedented octaalkyl dicarboxyl derivative 9,18-di(carboxymethyl)-4,13,14.23-tetraethyl-3,8,19,24-tetramethyl-25,26,27,28,29-pentazahexacyclo[20.2.1.1$^{2,5}$.1$^{7,10}$.1$^{12,15}$.1$^{17,20}$]nonacosa-2,4,6,8,10(28),11,13,15,17(26),18,20,22,24-tridecaene or 3,12,13,22-tetraethyl-8,17-di(carboxymethyl)-2,7,18,23-tetramethylsapphyrin.

BRIEF DESCRIPTION OF THE DRAWINGS

FIG. 1(1A-1C) schematically describes the synthetic methods of the present invention and particular sapphyrin products.

FIG. 5(5A-5D) shows the synthetic methods of the present invention and sapphyrin products.

DESCRIPTION OF THE PREFERRED EMBODIMENTS

Recently, in the context of parallel work in the "expanded porphyrin" area, ((a) Sessler, J. L.; Murai, T.; Lynch, V.; Cyr, M. *J. Am. Chem. Soc.* 1988, 110, 5586-5588; (b) Sessler, J. L.; Murai, T.; Lynch, V. *Inorg. Chem.* 1989, 28, 1333-1341; (c) Sessler, J. L.; Murai, Hemmi, G. *Inorg. Chem.* 1989, 28, 3390-3393) the present inventors have developed a simple, 3-step, high-yield synthesis of the dicarboxyl substituted tripyrrane 6, which involves as its key transformation the near-quantitative condensation between 3,4-diethylpyrrole 7 (Sessler, J. L.; Mozaffari, A.; Johnson, M. R. submitted to *Organic Syntheses*) and benzyl 5-(acetoxymethyl)-4-ethyl-3-methylpyrrole-2-carboxylate 8 (FIG. 1A) (Sessler, J. L.; Lynch V.; Johnson, M. R. *J. Org. Chem.* 1987, 52 4394-4397.) Therefore, for an improved synthesis of sapphyrins, an improved synthesis of the diformyl substituted bipyrrole component is necessary. Originally, the requisite diformyl bipyrrole was prepared from the direct Ullman coupling of a 5-iodo pyrrole-2-carboxylate and subsequent functionalization in analogy to that shown in FIG. 1B (Bauer, V. J.; Clive, D. R.; Dolphin, D.; Paine, J. B. III; Harris, F. L.; King, M. M.; Loder, J.; Wang, S.-W. C.; Woodward, R. B. *J. Am. Chem. Soc.* 1983, 105, 6429-6436) (Broadhurst, M. J.; Grigg, R.; Johnson, A. W. *J. Chem. Soc.* Perkin Trans. 1, 1972, 2111). However, the difficulty inherent in synthesizing the starting iodo pyrroles led to the use of a less direct but overall higher-yielding sequence involving Ullman coupling of a protected preformylated pyrrole. (Bauer, V. J.; Clive, D. R.; Dolphin, D.; Paine, J. B. III; Harris, F. L.; King, M. M.; Loder, J.; Wang, S.-W. C.; Woodward, R. B. *J. Am. Chem. Soc.* 1983, 105, 6429-6436). Recently, however, the present inventors have found that the Barton-Zard pyrrole synthesis (Barton, D. H. R.; Zard, S. Z.; *J. Chem. Soc. Chem. Comm.* 1985, 1098-1100) provides a facile means of preparing the alpha-free pyrrole 13 in >100 g lots. (Sessler, J. L.; Johnson, M. R.; Creager, S.; Fettinger, J.; Ibers, J. A. to be submitted to *J. Am. Chem. Soc.*). Given this notable advance, the original Woodward-Johnson bipyrrole synthesis has finally become synthetically viable. Iodination of pyrrole 13 (to give 14) (see FIG. 1B) followed by Ullman coupling in the presence of copper-bronze affords the bipyrrole 15 in roughly 50% overall yield. After saponification and decarboxylation (to give 16), standard Vilsmeier formylation affords the key bipyrrolic intermediate 5 in 60% yield (based on 15). Subsequent [3+2] condensation (Bauer, V. J.; Clive, D. R.; Dolphin, D.; Paine, J. B. III; Harris, F. L.; King, M. M.; Loder, J.; Wang, S.-W. C.; Woodward, R. B. *J. Am. Chem. Soc.* 1983, 105, 6429-6436) (Broadhurst, M. J.; Grigg, R.; Johnson, A. W. *J. Chem. Soc.* Perkin Trans. 1, 1972, 2111) between compounds 5 and 6 gave the decaalkyl sapphyrin 2 in 45% yield after chromatographic purification. When this same condensation was carried out with tripyrrane 12, sapphyrin 3, which may be saponified to produce the dicarboxyl substituted sapphyrin 4 or partially saponified to produce a monocarboxyl sapphyrin 4a, is obtained in roughly 40% overall yield based on 5.

A particular decaalkyl sapphyrin 2 produced by the present synthetic approach is analogous to the systems produced earlier. It differs, however, in the arrangement of the alkyl substituents about the macrocyclic periphery. Nonetheless, it remains a 22 pi-electron pentapyrrolic system and shows typical spectroscopic and reactivity features expected of a decaalkyl sapphyrin. For instance, the most stable form of this material is the diprotonated dicationic form, which as its dihydrochloride salt ([2·(2H+)]·2Cl−) in dilute CHCl3 solution exhibits an intense Soret-like band at 456 nm (log epsilon=5.7]) and two weaker Q-type bands at 624 nm (log epsilon=4.07) and 676 nm (log spsilon=4.15). (Maiya, B. G.; Harriman, A.; Cyr, M.; Sessler, J. L. *J. Phys. Chem.*, in press.) The 1H NMR spectrum of this dicationic material is also typical of a sapphyrin and provides further evidence for the original aromatic formulation. It displays, for instance, well resolved meso-like peaks at 11.66 and 11.70 ppm and internal pyrrole NH signals at −4.31, −4.64, and −4.97 ppm in a 2:1:2 ratio. However, in work that extends the earlier studies it has been found that both the neutral and dicationic (diprotonated) forms exist as monomers at low concentration in nonpolar media, such as chloroform, but undergo extensive dimerization at higher concentrations or in solvents of higher polarity, such as MeOH or CH3CN, as evidenced, in part, by a blue-shifting in the high-intensity Soret-like bands. (Judy, M. L.; Matthews, J. L.; Newman, J. T.; Skiles, H.; Boriack, R.; Cyr, M.; Maiya, B. G.; Sessler, J. L., submitted to *Photochem. Photobiol.*) (Maiya, B. G.; Harriman, A.; Cyr, M.; Sessler, J. L. *J. Phys. Chem.*, in press.)

Figure 2:
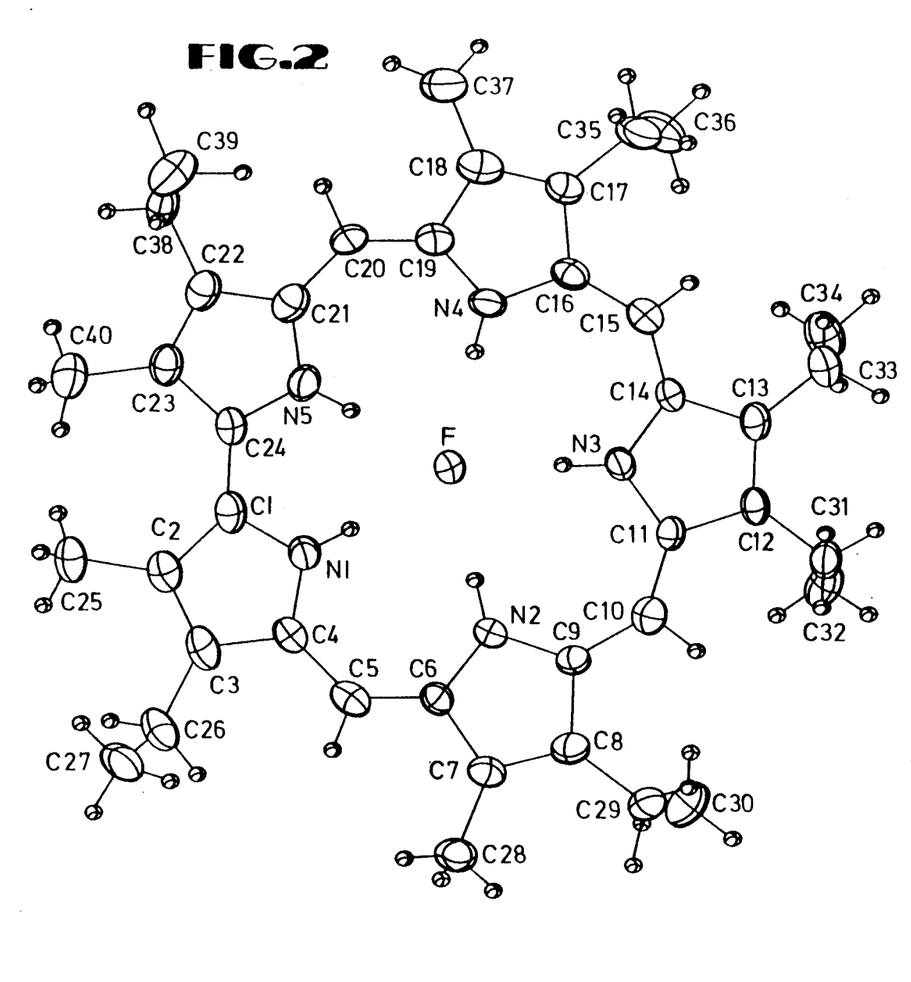
FIG. 2 shows the molecular structure of the [2·(2H+)·F−]+ cation showing the atom labeling scheme. Non-hydrogen atoms are drawn with 50% ellipsoids; H atoms are drawn artificially small. Details of the core geometry are in the specification.

X-ray quality single crystals of the diprotonated form of compound 2 were obtained by treating the free-base form in dichloromethane with aqueous HCl (to make the dihydrochloride salt), exchanging the chloride counter ions with AgPF6, and crystallizing by vapor diffusion with diethyl ether under non-anhydrous conditions. The material so obtained was assumed to be the bishexafluorophosphate salt of 2·(2H+) and to be strictly comparable to the dihydrochloride salt discussed above. However, the visible spectrum in chloroform showed features, including a blue-shifted Soret band, that were more characteristic of the dihydrochloride salt in methanol, (Maiya, B. G.; Harriman, A.; Cyr, M.; Sessler, J. L. *J. Phys. Chem.*, in press.) and the 1H NMR spectrum revealed pyrrolic NH signals at −7.35 and −6.20 ppm that were shifted to considerably higher field than those observed for [2·(2H+)]·2Cl−. In addition, the X-ray structure determination gave ([2·(2H+)·F−][PF6]; $C_{40}H_{51}F_7N_5P$; $C_{2h}^5-P2_1/c$; Z=4 in a cell of dimensions 1=9.148(1), b=26.880(2), c=15.229 Angstrom, beta-92.87(1)° at 160° K. The final model involved anisotropic refinement of all non-hydrogen atoms and isotropic refinement of hydrogen atoms and revealed only one $PF_6$ anion per sapphyrin cation. This cation displayed a central core in which there is a hydrogen atom attached to each of the five nitrogen atoms and a central peak (X) of electron density about that of a nitrogen atom. Since the five N—H···X bonds were nearly linear and about 2.7 Angstrom in length it is clear from simple stereochemical considerations (Hamilton, W. C.; Ibers, J. A. *Hydrogen Bonding in Solids*, W. A. Benjamin, New York, 1968) that X can correspond only to N, O, or F. The species X must be uninegative, and hence $OH^-$ and $F^-$ are possible. But the chemical sequence employed (involving an acidic wash) does not provide any obvious source of $OH^-$ and hence $F^-$ is more likely. According to the supplier (Alfa Products), the starting $AgPF_6$ contains up to ½ percent AgF as an impurity. Under the metathesis conditions (involving an excess of $AgPF_6$), this impurity could have served as the source of the observed, bound fluoride anion. Alternatively, it is possible that the $AgPF_6$ underwent hydrolysis to give HF, AgOH, $H_3PO_4$, etc., during the course of crystallization. Although not a proof, the structural data refine better with X as F rather than O). The resultant structure (FIG. 2) shows N···F distances ranging from 2.697(3) to 2.788(3) Angstrom, N—H distances ranging from 0.83(3) to 0.92(4) Angstrom and N—H···F angles ranging from 167(2) to 177(3)°. The five N atoms and the central F atom are essentially planar (average deviation, 0.03 Angstrom) and no H atom deviates by more than 0.14 Angstrom from this plane. Thus, from the X-ray results and the chemistry involved the determined structure is best formulated as the mixed hexafluorophosphate fluoride salt of 2, $[2\cdot(2H^+)\cdot F^-][PF_6^-]$. Consistent with this interpretation is the observation of signals in the $^{19}F$ NMR spectrum ascribable to both $PF_6$ (at delta = −73.9) and $F^-$ (at delta = −153.7 and −153.8, in a ca. 1:4 ratio), and the finding that the dihydrofluoride salt of $2([2\cdot(2H^+)\cdot F^-]\cdot F^-)$ (prepared independently) gives rise to essentially identical $^1H$ NMR, laser desorption MS, and optical spectra as did the crystallographically characterized material and shows bound fluoride anion signals at −153.4 and 153.5 ppm in the $^{19}F$ NMR spectrum.

The binding of a species such as $F^-$ centrally within the core of the 18 pi-electron porphyrin system is not possible as the trans nitrogen distances (at about 4 Angstrom[18]) are too short. The present 22 pi-electron sapphyrin system has a core size of roughly 5.5 Angstrom diameter and is nicely suited to the binding of a central moiety about the size of the $F^-$ ion with appropriate strong hydrogen bonding interactions. As such, the fully protonated sapphyrin 2 stands as a new example of a rapidly increasing class of anion receptors. (For overviews of anion binding receptors see: (a) Lindoy, L. F. *The Chemistry of Macrocyclic Ligands*, Cambridge University Press, Cambridge, 1989, Chapter 5; (b) Lehn, J.-M. *Angew. Chem., Int. Ed. Engl.*, 1988, 27, 89–112; (c) Potvin, p. G.; Lehn, J.-M. in *Synthesis of Macrocycles* (*Progress in Macrocyclic Chemistry, Vol.* 3), Izatt, R. M.; Christensen, J. J., Eds., Wiley, New York, 1987, pp. 167–239; (d) Vogtle, F.; Sieger, H.; Muller, W. M. *Top. Current Chem.* 1981, 98, 107–161; (e) Kimura, E. *Top. Current Chem.*, 1981, 128, 113–141; (f) Schmidtchen, F. P. *Top. Current Chem.*, 1986, 132, 101–133. For examples of specific fluoride anion complexing agents see: (a) Graf, E.; Lehn, J.-M. *J. Am. Chem. Soc.* 1976, 98, 6403–6405; (b) Suet, E.; Handel, H. *Tetrahedron Lett.* 1984, 25, 645–648; (c) Dietrich, B.; Guilhem, J.; Hehn, J.-M.; Pascard, C.; Sonveaux, E. *Helv. Chim. Acta* 1984, 67, 91–104; (d) Newcomb, M.; Blanda, M. T. *Tetrahedron Lett.* 1988, 29, 4261–4264.) Preliminary experiments carried out in mixed $CD_2Cl_2/CD_3OD$ indicate that the bound fluoride anion is labile on the $^{19}F$ NMR time scale, undergoing rapid exchange with free fluoride anion in solution. Currently, work is being devoted to studying this exchange process in greater detail and to exploring the extent to which the protonated sapphyrins may serve as binding agents for other small anions and neutral molecules.

The decaalkyl sapphyrins described herein have already and should prove further to be of particular use because of, for example, their ready solubility in solvents such as chloroform, and/or methanol and potentially in phospholipid structures of liposomes or of organisms. The carboxylated sapphyrins and dioxosapphyrins described herein may be of particular use because of their unprecedented aqueous solubility and ability to be coupled to solid matrices or biological molecules such as antibodies.

A method according to the present invention for producing a particular alkyl substituted sapphyrin comprises the following steps:

(A) reacting propionaldehyde and nitroethane to produce 4-nitro-3-pentanol;

(B) reacting 4-nitro-3-pentanol with acetic anhydride to form 3-acetoxy-2-nitropentane;

(C) reacting 3-acetoxy-2-nitropentane with ethyl isocyanoacetate in the presence of a nonnucleophilic base to form ethyl 3-ethyl-4-methylpyrrole-2-carboxylate;

(D) reacting ethyl 3-ethyl-4-methylpyrrole-2-carboxylate with iodine and iodide to form ethyl 3-ethyl-5-iodo-4-methylpyrrole-2-carboxylate;

(E) coupling two molecular equivalents of ethyl 3-ethyl-5-iodo-4-methylpyrrole-2-carboxylate in the presence of copper bronze to produce diethyl 4,4'-diethyl-3,3'-dimethyl-2,2'-bipyrrole-5,5'-dicarboxylate;

(F) converting diethyl 4,4'-diethyl-3,3'-dimethyl-2,2'-bipyrrole-5,5'-dicarboxylate to 4,4'-diethyl-3,3'-dimethyl-2,2'-bipyrrole by saponification and decarboxylation;

(G) reacting 4,4'-diethyl-3,3'-dimethyl-2,2'-bipyrrole with dimethylformamide and phosphorus oxychloride to form 4,4'-diethyl-5,5'-diformyl-3,3'-dimethyl-2,2'-bipyrrole;

(H) condensing 3,4-diethylpyrrole with two molecular equivalents of benzyl 5-(acetoxymethyl)-4-ethyl-3-methylpyrrole-2-carboxylate to produce 2,5-bis(5-benzyloxycarbonyl-3-ethyl-4-methylpyrrol-2-ylmethyl)-3,4-diethylpyrrole;

(I) hydrogenating 2,5-bis(5-benzyloxycarbonyl-3-ethyl-4-methylpyrrol-2-ylmethyl)-3,4-diethylpyrrole to produce 2,5-bis(5-carboxy-3-ethyl-4-methylpyrrol-2-ylmethyl)-3,4-diethylpyrrole; and (J) condensing 4,4'-diethyl-5,5'-diformyl-3,3'-dimethyl-2,2'-bipyrrole and 2,5-bis(5-carboxy-3-ethyl-4-methylpyrrol-2-ylmethyl)-3,4-diethylpyrrole to produce 3,8,12,13,17,22-hexaethyl-2,7,18,23-tetramethylsapphyrin.

A method for producing a carboxy substituted sapphyrin according to the present invention comprises the steps of:

(A) reacting propionaldehyde and nitroethane to produce 4-nitro-3-pentanol;

(B) reacting 4-nitro-3-pentanol with acetic anhydride to form 3-acetoxy-2-nitropentane;

(C) reacting 3-acetoxy-2-nitropentane with ethyl isocyanoacetate in the presence of a nonnucleophilic base to form ethyl 3-ethyl-4-methylpyrrole-2-carboxylate;

(D) reacting ethyl 3-ethyl-4-methylpyrrole-2-carboxylate with iodine and iodide to form ethyl 3-ethyl-5-iodo-4-methylpyrrole-2-carboxylate;

(E) coupling two molecular equivalents of ethyl 3-ethyl-5-iodo-4-methylpyrrole-2-carboxylate in the presence of copper bronze to produce diethyl 4,4'-diethyl-3,3'-dimethyl-2,2'-bipyrrole-5,5'-dicarboxylate;

(F) converting diethyl 4,4'-diethyl-3,3'-dimethyl-2,2'-bipyrrole-5,5'-dicarboxylate to 4,4'-diethyl-3,3'-dimethyl-2,2'-bipyrrole by saponification and decarboxylation;

(G) reacting 4,4'-diethyl-3,3'-dimethyl-2,2'-bipyrrole with dimethylformamide and phosphorus oxychloride to form 4,4'-diethyl-5,5'-diformyl-3,3'-dimethyl-2,2'-bipyrrole;

(H) reacting benzyl 4-ethoxycarboxylmethyl-3,5-dimethylpyrrole-2-carboxylate with lead tetraacetate to produce benzyl 5-(acetoxymethyl)-4-ethoxycarbonylmethyl-3-methylpyrrole-2-carboxylate;

(I) condensing 3,4-diethylpyrrole with two molecular equivalents of 5-(acetoxymethyl)-3-ethoxycarbonylmethyl-4-methylpyrrole-2-carboxylate under acidic conditions to produce 2,5-bis(5-benzyloxycarbonyl-3-ethoxycarbonylmethyl-4-methylpyrrol-2-ylmethyl)-3,4-diethylpyrrole;

(J) hydrogenating 2,5-bis(5-benzyloxycarbonyl-3-ethoxycarbonylmethyl-4-methylpyrrol-2-ylmethyl)-3,4-diethylpyrrole to produce 2,5-bis(5-carboxy-3-ethoxycarbonylmethyl-4-methylpyrrol-2-ylmethyl)-3,4-diethylpyrrole;

(K)
(a) condensing 4,4'-diethyl-5,5'-diformyl-3,3'-dimethyl-2,2'-bipyrrole and 2,5-bis(5-carboxy-3-ethoxycarbonylmethyl-4-methylpyrrol-2-ylmethyl)-3,4,diethylpyrrole to produce 3,12,13,22-tetraethyl-8,17-di(ethoxycarbonylmethyl)-2,7,18,23-tetramethylsapphyrin; and
(b) producing 3,12,13,22-tetraethyl-8,17-di(ethoxycarbonylmethyl)-2,7,18,23-tetramethylsapphyrin as described in step (K)(a) and saponifying it to produce 3,12,13,22-tetraethyl-8,17-di(carboxymethyl)-2,7,18,23-tetramethylsapphyrin; or
(c) producing 3,12,13,22-tetraethyl-8,17-di(ethoxycarbonylmethyl)-2,7,18,23-tetramethylsapphyrin as described in step (K)(a) and partially saponifying it to produce 3,12,13,22-tetraethyl-8-(ethoxycarbonylmethyl)-17-(carboxymethyl)-2,17,18,23-tetramethylsapphyrin or 3,12,13,22-tetraethyl-8-(carboxymethyl)-17-(ethoxycarbonylmethyl)-2,7,18,23-tetramethylsapphyrin.

A representation of a sapphyrin compound of the present invention is shown in FIG. 3. In FIG. 3 $D_a$, $D_b$, $D_c$, $D_d$, $D_e$ and $D_f$ are independently alkanes, one or more functionalized alkanes, derivatized alkanes or derivatized functional alkanes and at least three of $D_a$, $D_b$, $D_c$, $D_e$ and $D_f$ comprise an alkane having two or more carbon atoms. The functionalized alkanes includes alkanes with one or more chemically reactive amino, hydroxyl, carboxyl, carbonyl, cyanate, isocyanate, thiocyanate, sulfhydryl, nitrile, diazo, iodide, disulfide or sulfonic substituents. Analogous functionalized alkanes are of course known to those of skill in the art and considered to be within the original grouping. The derivatized alkanes includes alkanes with an alkenyl, alkynyl, aryl, cycloalkyl or halide (other than iodide) substituent. A derivatized functional alkanes includes amides, esters, ethers or disulfide substituents.

Specific compounds herein are described by the compound of FIG. 3 where $D_a$, $D_d$, $D_e$ and $D_f$ are ethyl; and $D_b$ is methyl; where $D_a$, $D_e$, and $D_f$, are ethyl; $D_b$ is methyl; and $D_d$ is $CH_2CO_2Et$; where $D_a$, $D_e$ and $D_f$ are ethyl; $D_b$ is methyl and $D_d$ is $CH_2CO_2H$; or where $D_a$, $D_e$ and $D_f$ are ethyl; $D_b$ is methyl; one $D_d$ is $CH_2CO_2H$; and one $D_d$ is $CH_2CO_2Et$.

The present invention also includes methods for synthesizing substituted dioxosapphyrins. One such method comprises the steps of:

(a) reacting furfuraldehyde and palladium acetate to produce 5,5'-diformyl-2,2'-bifuran;
(b) condensing 3,4-diethylpyrrole with two molecular equivalents of benzyl-5-(acetoxymethyl)-4-ethyl-3-methylpyrrole-2-carboxylate to produce 2,5-bis(5-benzyloxycarbonyl-3-ethyl-4-methylpyrrol-2-ylmethyl)-3,4-diethylpyrrole;
(c) hydrogenating 2,5-bis(5-benzyloxycarbonyl-3-ethyl-4-methylpyrrol-2-ylmethyl)-3,4-diethylpyrrole to produce 2,5-bis(5-carboxy-3-ethyl-4-methylpyrrol-2-ylmethyl-3,4-diethylpyrrole; and
(d) reacting 5,5'-diformyl-2,2'-bifuran and 2,5-bis(5-carboxy-3-ethyl-4-methylpyrrol-2-ylmethyl)-3,4-diethylpyrrole to produce 8,12,13,17-tetraethyl-7,18-dimethyldioxosapphyrin.

Carboxy substituted dioxosapphyrins may also be synthesized according to the present invention by a process comprising the steps of:

(A) reacting benzyl 4-ethoxycarbonylmethyl-3,5-dimethylpyrrole-2-carboxylate with lead tetraacetate to produce benzyl 5-(acetoxymethyl)-4-ethoxycarbonylmethyl-3-methylpyrrole-2-carboxylate;
(B) condensing two molecular equivalents of benzyl 5-(acetoxymethyl)-4-ethoxycarbonylmethyl-3-methylpyrrole-2-carboxylate with 3,4-diethyl pyrrole under acidic conditions to produce 2,5-bis(5-benzyloxycarbonyl-3-ethoxycarbonylmethyl-4-methylpyrrol-2-ylmethyl)-3,4-diethylpyrrole;
(C) hydrogenating 2,5-bis(5-benzyloxycarbonyl-3-ethoxycarbonylmethyl-4-methylpyrrol-2-ylmethyl)-3,4-diethylpyrrole to produce 2,5-bis(5-carboxy-3-ethoxycarbonylmethyl-4-methylpyrrol-2-ylmethyl)-3,4-diethylpyrrole; and
(D) reacting furfuraldehyde and palladium acetate to produce 5,5'-diformyl-2,2'-bifuran; and
(E) condensing 5,5'-diformyl-2,2'-bifuran and 2,5-bis(5-carboxy-3-ethoxycarbonylmethyl-4-methylpyrrol-2-ylmethyl)-3,4-diethylpyrrole to produce 8,17-diethoxycarbonylmethyl-12,13-diethyl-7,18-dimethyldioxosapphyrin.

EXAMPLE 1

Specific Synthetic Methods

4-Nitro-3-pentanol (Kambe, S., Yasuda, H.; *Bull. Chem. Soc. Japn.* 1968, 41, 1444–1446.) Propionaldehyde (174 g, 3 mol), isopropyl alcohol (400 ml) and finely ground potassium fluoride (25 g, 0.15 mol) were added to a 3-necked round bottomed flask equipped with a mechanical stirrer, a thermometer, a dropping funnel, and a drying tube. Nitroethane (225.2 g. 3 mol) was added dropwise with stirring, keeping the temperature below 40° C. with the aid of an ice bath. Fairly vigorous stirring was continued for 24 hours. The catalyst was then removed by filtration and the filtrate concentrated under reduced pressure. The residue was poured into water (500 ml) and the oil extracted with ether (3×300 mL). The ethereal layer was then dried over anhydrous $Na_2SO_4$, and the solvent removed under reduced pressure. The remaining liquid was distilled in vacuo and the fraction boiling at 82°–84° C./5 torr was collected in a tared 1-liter roundbottom flask to afford 4-nitro-3-pentanol (320 g, 2.4 moles, 80%). The flask containing the product was used directly in the next step.

3-Acetoxy-2-nitropentane (Tindall, J. B. *Ind. & Eng. Chem.* 1941, 33, 65.) To the above flask, containing 4-nitro-3-pentanol (320 g, 2.4 moles), was added an eggshaped stirrer and 1 ml concentrated sulfuric acid. The contents of the flask were then stirred in an ice bath and acetic anhydride (255 g, 2.5 moles) was added in portions, keeping the temperature of the reactants below 60° C. When the addition of acetic anhydride was complete, the contents of the flask were stirred for an additional hour. The flask was then equipped for vacuum distillation. The lower boiling components ($Ac_2O$ and AcOH) were removed using a water aspirator and gently heating ($\leq 100°$ C. bath temperature) the stirred contents of the flask. After these byproducts were removed, the system was cooled, hooked up to a vacuum pump, and carefully heated. The fraction boiling at 90° C./5 torr was collected, affording 3-acetoxy-2-nitropentane (370 g, 2.1 moles, 89%).

Ethyl 3-ethyl-4-methylpyrrole-2-carboxylate (13) (alternatively named 2-Ethoxycarbonyl-3-ethyl-4-methylpyrrole). To a stirred solution of 3-acetoxy-2-nitropentane (182.3 g, 1.04 mole) and ethyl isocyanoacetate (98 g, 0.87 mole) in THF (620 ml)/IPA (250 ml) was added 1,8-diazabicyclo[5,10]undec-7-ene (DBU) (294 g, 1.93 mole) portionwise with cooling in an ice bath so as to maintain a temperature of 20° C. to 30° C. at all times. When the DBU addition was complete the orange solution was stirred for 4 hours at room temperature. The solution was then filtered to remove the nitrite salt and the solvent removed on the rotary evaporator (50° C. bath temp, water aspirator). The residue was poured into a 1 L beaker and diluted with acetic acid (60 g, 1 mole), followed by warm water (350 ml). Additional water was then added to the point where the solution remained cloudy, even after thorough stirring. Methanol (150 ml) was then added, and the clear solution thus obtained was covered and placed in the freezer for twelve hours. The resulting precipitate was collected by filtration through a Buchner funnel, washed with 60/40 v/v water/methanol (3×200 ml), and dried to give the crude product as white flakes (102.3 g, 65%), mp 73°–75° C. This crude product may be used as is, or recrystallized from methanol to give pure material, mp 76° C. (lit. Franck, B.; Bringmann, G.; Wegner, C.; Spirgel, U. *Justus Liebigs Ann. Chem.* 1980, 263–274: 76° C.).

Ethyl 3-ethyl-5-iodo-4-methylpyrrole-2-carboxylate (14). This procedure is an adaptation of a general iodopyrrole formation procedure (Collman, J. P.; Chong, A. O.; Jameson, G. B.; Oakley R. T.; Rose, E.; Schmittou, E. R.; Ibers, J. A. *J. Am. .Chem. Soc.* 1981, 103, 516–533) where pyrrole (13) has been substituted for ethyl 5-carboxy-3-ethyl-4-methylpyrrole-2-carboxyate. A solution of $NaHCO_3$ (15.7 g, 0.19 mol) in 60 ml $H_2O$ was heated to 50° C. in a 1 L round bottom flask. To this was added 700 ml of 1,2-dichloroethane followed by ethyl 3-ethyl-4-methylpyrrole-2-carboxylate (13) (Barton, D. H. R.; Zard, S. Z. *J. Chem. Soc. Chem. Comm.* 1985, 1098–1100. Sessler, J. L.; Johnson, M. R.; Creager, S.; Fettinger, J.; Ibers J. A. to be submitted to *J. Am. Chem. Soc.*) (10 g, 55 mmol). A solution of $I_2$ (15.7 g, 62 mmol) and NaI (19.8 g, 0.13 mol) in 60 ml $H_2O$ was then added portionwise to the mixture over a 5 minute period. Undissolved $I_2$ was washed into the mixture with $H_2O$ and the resulting mixture was heated at reflux for one hour. The mixture was then cooled to room temperature and crystalline $Na_2S_2O_3$ (4 g) added to discharge excess iodine. The mixture was then transferred to a separatory funnel, the organic layer separated, and the aqueous phase washed with $CHCl_3$ (3×50 ml). The combined organic layers were washed with a 5% solution of $Na_2S_2O_3$ (3×50 ml), a 5% solution of $NaHCO_3$ (3×50 ml), a saturated brine solution (3×50 ml), and dried over $Na_2SO_4$ before the solvent was removed on the rotorary evaporator to leave an off-white solid which was recrystallized from $CH_2Cl_2$/hexanes giving a first crop of 11.8 g (70%) with m.p. 122°–124° C. (lit. Collman, J. P.; Chong, A. O.; Jameson, G. B.; Oakley R. T.; Rose, E.; Schmittou, E. R.; Ibers, J. A. *J. Am. Chem. Soc.* 1981, 103, 516–533 m.p. 120°–121° C.).

Figure 1A:
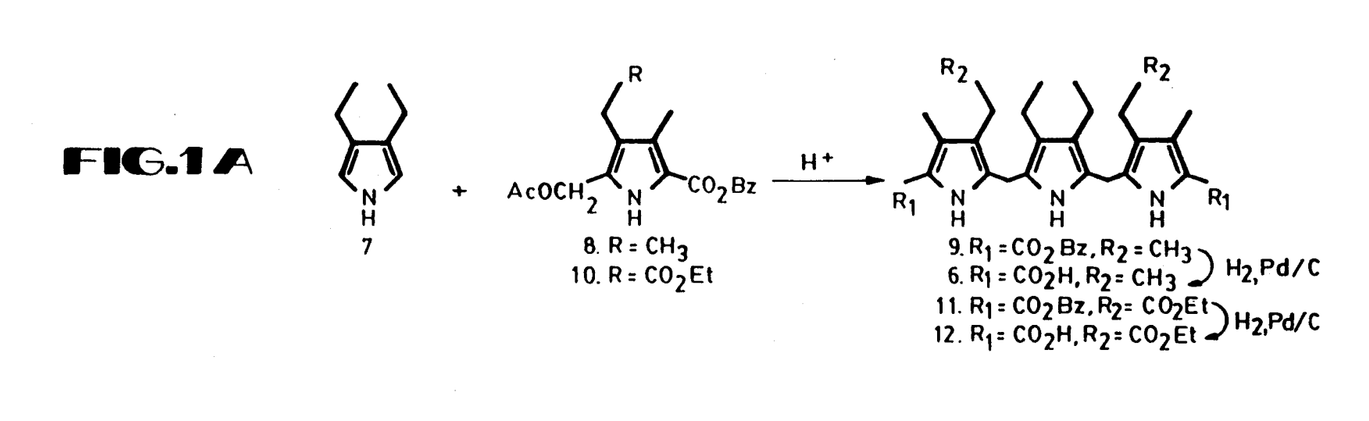
Figure 1B:
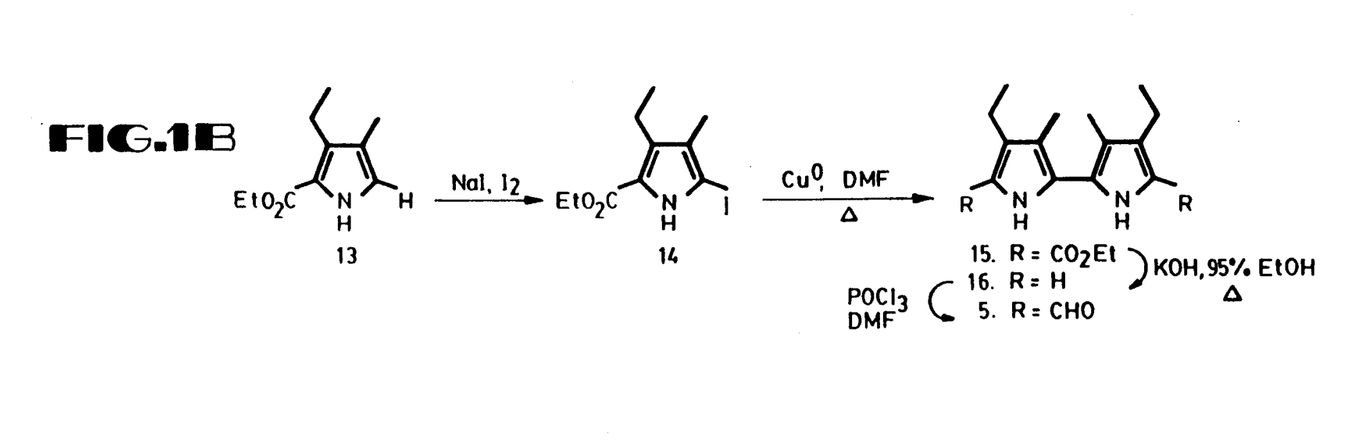
Figure 1C:
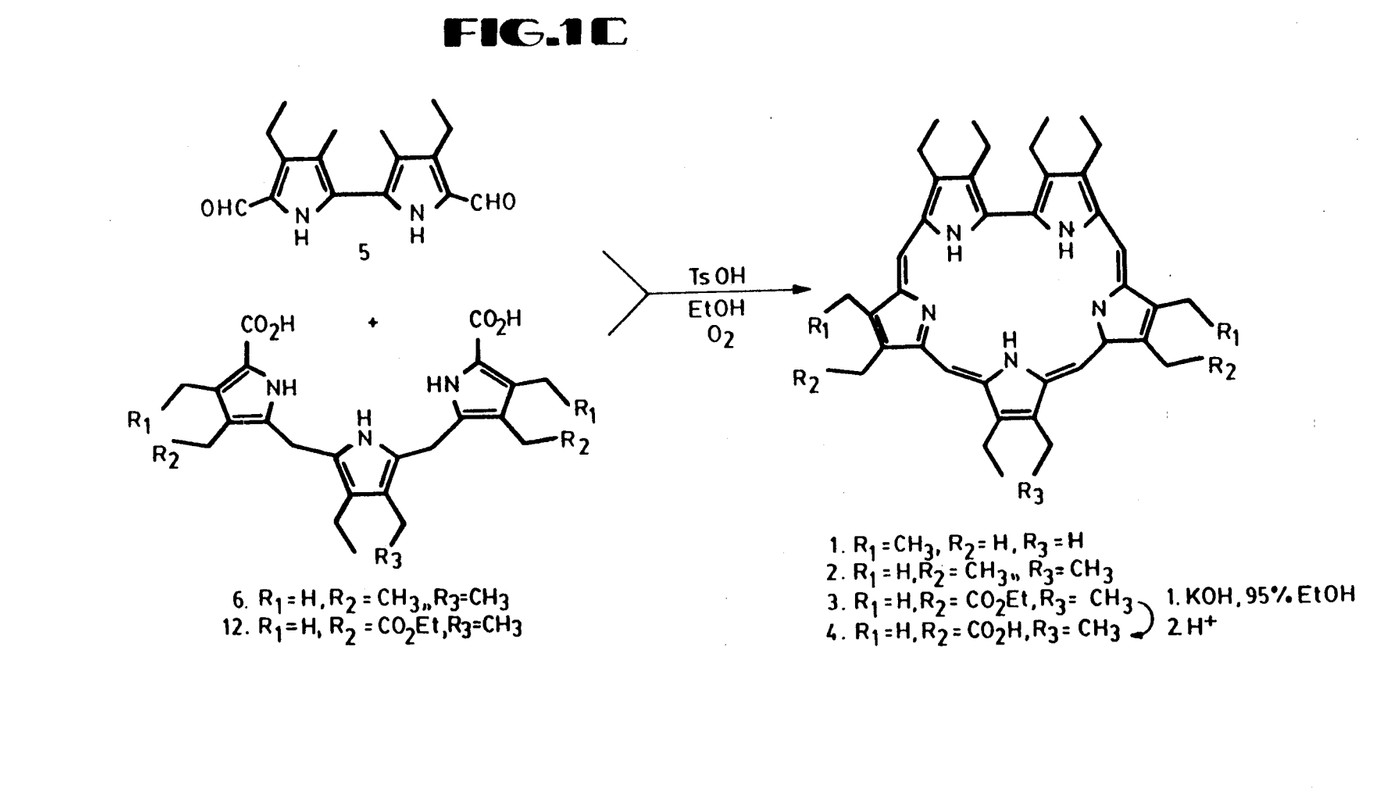

Diethyl 4,4'-diethyl-3,3'-dimethyl-2,2'-bipyrrole-5,5'-dicarboxylate (15) (see FIG. 1 for compound numbered structures). Ethyl 3-ethyl-5-iodo-4-methylpyrrole-2-carboxylate (14) (18.42 g, 0.06 mol) was dissolved in 120 ml of DMF. Copper bronze (18.5 g, Aldrich) was added and the mixture heated to 140° C. for one hour. If the mixture clotted during the course of the reaction, small crystals of $I_2$ were added until the clots redissolved. After the required time, the mixture was filtered through Celite to remove the copper, which was washed with hot $CHCl_3$ until the washings were colorless. The filtrate was then washed with 1N HCl (3×100 ml), 10% aqueous sodium thiosulfate (3×100 ml), and saturated brine (3×100 ml). The solution was dried over $Na_2SO_4$ before the solvent was removed on the rotorary evaporator to leave an oil. Pentane (ca. 100 ml) was added, and the mixture placed in the refrigerator for a few hours. The product precipitated out as white plates which were collected by filtration and washed with hexanes. The mother liquor can be chromatographed over silica gel to recover a small amount of additional bipyrrole as well as a modest quantity of starting ethyl 3-ethyl-4-methylpyrrole-2-carboxylate (13) (5.6 g, 0.03 mol). Thus, based on the amount of recovered (13) the yield of (15) is 6.48 g (50%). Further purification can be accomplished by recrystallization from $CH_2Cl_2$/hexanes: m.p. 178°–181° C.; $^1H$ NMR ($CDCl_3$) delta 1.15 (6H, t, J=7.36 Hz, $CH_2CH_3$), 1.36 (6 H, t, J=6.91 Hz $OCH_2CH_3$), 2.06 (6 H, s, $CH_3$), 2.79 (4 H, q, J=7.34 Hz $CH_2CH_3$), 4.32 (4 H, q, J=7.10 Hz, $OCH_2CH_3$), 871 (2 H, s, NH); MS, m/e (relative intensity) 360 (100), 314 (48.6), 267 (11.6), 240 (28.2); HRMS, 360.2059 (calcd for $C_{20}H_{28}N_2O_4$: 360.2049).

4,4'-Diethyl-3,3'-dimethyl-2,2'-bipyrrole (16) and 4,4'-diethyl-5,5'-diformyl-3,3'-dimethyl-2,2'-bipyrrole (5). Diethyl 4,4'-diethyl-3,3'-dimethyl-3,3'-bipyrrole-5,5'-dicarboxylate (15) (0.54 g, 1.5 mmol) is saponified and decarboxylated in ethylene glycol (10 ml) by heating at 180° C. (oil bath) in the presence of NaOH (99 mg 2.3 mmol) under $N_2$ until no starting material or sodium salts of bipyrrole carboxylates were present (as indicated by TLC). After cooling, the contents of the flask are diluted with water (10 ml) and extracted with $CHCl_3$ (3×15 ml). The combined $CHCl_3$ extracts were then dried over $Na_2SO_4$ and the solvent removed on the rotary evaporator to give compound 16 (0.201 g, 62%) as a solid which was carried quickly on to the formylation step since this product darkens upon standing: $^1$H NMR (CDCl$_3$) delta 1.22 (6 H, t, J=7.40 Hz, CH$_2$CH$_3$), 2.02 (6 H, s, CH$_3$), 2.48 (4 H, q, J=7.50 Hz, CH$_2$CH$_3$), 6.55 (2 H, s, alpha-H) 7.73(2H, s, NH); MS, M/e (relative intensity) 216 (100), 201 (53.3), 187 (15.7), 171 (10.4). 4,4'-Diethyl-3,3'-dimethyl-2,2'-bipyrrole (16) (1.28 g, 6 mmol) was dissolved in dry DMF (40 ml, 0.52 mol) under N$_2$. Freshly distilled phosphorus oxychloride (POCl$_3$) (4 ml, 43 mmol) was added dropwise with stirring. After addition of all the POCl$_3$, the resulting mixture was heated to 100° C. for 2 hours, and then cooled to room temperature. The solution was then poured into cold water (100 ml) and a 10% solution of NaOH added (ca. 60 ml) until a smell of amine was apparent. The precipitate was collected, washed with water, and dried in vacuo to yield 0.95 g (59%) of 5: m.p. 241°–242° C., $^1$H NMR (CDCl$_3$) delta 1.25 (6 H, t, J=7.50 Hz, CH$_2$CH$_3$), 2.12 (6H, s, CH$_3$), 2.78 (4 H, q, J=7.50 Hz, CH$_2$CH$_3$), 9.67 (2 H, s, NH) 9.96 (2 H, s, CHO); MS (relative intensity) 272 (100), 244 (39.2), 165 (26.0); HRMS, 272.1530 (calcd. For C$_{16}$H$_{20}$N$_2$O$_2$: 272.1525).

Benzyl 5-(acetoxymethyl)-4-ethoxycarbonylmethyl-3-methylpyrrole-2-carboxylate (10). Benzyl 4-ethoxycarbonylmethyl-3,5-dimethylpyrrole-2-carboxylate (Johnson, A. W.; Markham, E.; Price, R.; Shaw, K. B. *J. Chem. Soc.* 1958, 4254–4257. (60.2 g. 0.191 mol) was dissolved in glacial acetic acid (440 ml). Lead tetraacetate (90 g. 0.204 mol) was added all at once and the mixture was stirred for two hours. The mixture was poured into water (750 ml) with vigorous stirring. The precipitate was collected by filtration, washed with water and air dried to give crude 10 (62.1 g, 87%), which was recrystallized from CH$_2$Cl$_2$/hexanes to give pure product: m.p. 117°–119° C., $^1$H NMR (CDCl$_3$) delta 1.24 (3 H, t, J=7.09 Hz OCH$_2$CH$_3$) 2.06 (3H, s, C(O)CH$_3$), 2.29 (3 H, s, beta-CH$_3$), 3.47 (2 H, s, CH$_2$CO$_2$Et), 4.12 (2 H, q, J=7.12 Hz, OCH$_2$CH$_3$), 5.06 (2 H, s, alpha-CH$_2$OCOCH$_3$), 5.31 (2 H, s, CH$_2$Ph), 7.30–7.43 (5 H, m, aromatic), 9.08 (1 H, s, NH); MS (relative intensity) 373 (71.7), 314(33.3), 240 (54.3), 222 (95.0), 91 (100), 60 (69.4), 45 (69.1), 43 (79.3); HRMS, 373.1536 (calcd for C$_{20}$H$_{23}$NO$_6$: 373.1525).

2,5-Bis-(5-benzyloxycarbonyl-3-ethoxycarbonylmethyl-4-methylpyrrol-2-ylmethyl)-3,4-diethylpyrrole (11). 3,4-Diethylpyrrole (Sessler, J. L.; Mozaffari, A.; Johnson, M. R. submitted to *Organic Syntheses*) (7) (0.62 g, 5.0 mmol), benzyl 5-(acetoxymethyl)-3-ethoxycarbonylmethyl-4-methylpyrrole-2-carboxylate (10) (3.94 g, 10.6 mmol), and p-toluenesulfonic acid monohydrate (152 mg) were dissolved in 50 ml of absolute ethanol and heated at reflux for 4 hours under N$_2$. The resulting suspension was reduced in volume to 30 ml and placed in the freezer for several hours. The product was then collected by filtration, washed with a small amount of cold ethanol, and recrystallized from CH$_2$Cl$_2$/ethanol to afford compound 11 as a fine, off-white powder (2.13 g, 50%); m.p. 127°–128° C.; 1H NMR (CDCl$_3$) delta 1.28 (6 H, t, J=7.47 HZ, CH$_2$CH$_3$), 1.20 (6 H, t, J=7.07 Hz, OCH$_2$CH$_3$), 2.26 (6 H, s, CH$_3$), 2.48 (4 H, q, J=7.34 HZ, CH$_2$CH$_3$), 3.31 (4 H, s, CH$_2$CO$_2$Et), 3.70 (4 H, s, pyrrole$_2$-CH$_2$), 4.05 (4 H, q, J=7.09 Hz, OCH$_2$CH$_3$), 4.75 (4 H, br s, CH$_2$Ph), 7.14–7.32 (10 H, m, aromatic), 8.83 (1 H, s, NH), 11.5 (2 H, br s, NH); CIMS, (M+H)$^+$ 778.6; HRMS, 749.3689 (calcd for C$_{44}$H$_{51}$N$_3$O$_8$: 749.3676).

2,5-Bis(5-carboxy-3-ethoxycarbonylmethyl-4-methylpyrrol-2-ylmethyl)-3,4-diethylpyrrole (12). 2,5-Bis(5-benzyloxycarbonyl-3-ethoxycarbonylmethyl-4-methylpyrrol-2-ylmethyl)-3,4-diethylpyrrole (11) (0.75 g, 1 mmol) was dissolved in 85 ml of dry THF and hydrogenated over 10% palladium-charcoal (41 mg) at 1 atm H$_2$ until the reaction was deemed complete as judged by TLC. The catalyst was then separated by filtration, the solvent reduced in volume on the rotary evaporator, and the product precipitated by trituration with n-heptane. The white precipitate was collected by filtration and dried in vacuo to yield 0.56 g (98%) of 12 (m.p. 149° C. (dec.)), which was then used directly in the next step (the synthesis of 3, vide infra) without further purification.

3,8,12,13,17,22-Hexaethyl-2,17,18,23-tetramethylsapphyrin (2). 4,4'-Diethyl-5,5'-diformyl-3,3'-dimethyl-2,2'-bipyrrole (5) (476 mg, 1.72 mmol) and 2,5-bis(5-carboxy-3-ethyl-4-methylpyrrol-2-ylmethyl)-3,4-diethylpyrrole (6) (Sessler, J. L.; Lynch, V.; Johnson, M. R. *J. Org. Chem.* 1987, 52, 4394–4397) (800 mg, 1.77 mmol) were dissolved in 1.75 L of absolute ethanol with the aid of a heat gun. The mixture was allowed to cool to room temperature before 1.3 g of p-toluenesulfonic acid monohydrate was added all at once. Prehumidified (i.e. ethanol saturated) oxygen was then bubbled through the mixture for 18 hours with good stirring. The ethanol was then removed on the rotorary evaporator, the green-blue residue taken up in CHCl$_3$ and purified by column chromatography (Merck type 60 (230–400) mesh Silica gel) using MeOH/CHCl$_3$ 5/95 as eluent and collecting the dark green fraction. Removal of the solvent gave 460 mg (44%) of (2) which can be purified further by recrystallizing from CHCl$_3$/hexanes. $^1$H NMR (CDCl$_3$) delta −1.59 (7H, br s, NH+2H$_2$O), 1.95 (6 H, t, J=7.46 Hz, CH$_2$CH$_3$), 2.10 (6 H, t, J=7.71 Hz, CH$_2$CH$_3$), 2.14 (6 H, t, J=7.81 Hz, CH$_2$CH$_3$), 3.88 (6 H, s, CH$_3$), 3.98 (6 H, s, CH$_3$), 4.30 (4 H, q, J=7.90 Hz, CH$_2$CH$_3$), 4.48 (4 H, q, J=8.23 Hz, CH$_2$CH$_3$), 4.53 (4 H, q, J=7.65 Hz, CH$_2$CH$_3$), 10.83 (2 H, s, meso-H), 10.88 (2 H, s, meso-H); Vis (CHCl$_3$)=456, 626, 668, 714 nm. For [2·(2H+)]$^{2+}$·[2Cl$^-$]$^{2-}$, $^1$H NMR (CDCl$_3$) delta −4.97 (2 H, s, NH), −4.64 (1 H, s, NH), −4.31 (2 H, s, NH), 2.18–2.34 (9 H, m, CH$_2$CH$_3$), 4.13 (6 H, s, CH$_3$), 4.24 (6 H, s, CH$_3$), 4.56 (4 H, q, J=7.68 Hz, CH$_2$CH$_3$), 4.69–4.75 (8 H, m, CH$_2$CH$_3$), 11.67 (2 H, s, meso-H), 11.71 (2 H, s, meso-H); HRMS, 601.4136 (calcd for C$_{40}$H$_{51}$N$_5$: 601.4144); Vis lambda-$_{max}$ (CHCl$_3$) 455,577, 623, 675, 687 nm. For [2·(2H+)]$^{2+}$·[2F$^-$]$^{2-}$ $^1$H NMR (CD$_2$Cl$_2$) delta −8.44 (4 H, br s, NH), −7.12 (1 H, br s, NH), 2.06–2.19 (18 H, m, CH$_2$CH$_3$), 4.25 (6 H, s, CH$_3$), 4.28 (6 H, s, CH3), 4.66–4.78 (12 H, m, CH$_2$CH$_3$), 11.16 (2 H, s, meso-H), 11.24 (2 H, s, meso-H); $^{19}$F NMR (CD$_2$Cl$_2$) delta −153.4, −153.5 (ca. 1:4 ratio, F$^-$); Laser Desorption MS, 600 ([M+H]$^+$), 620 ([M=H+HF]$^+$); Vis lambda-$_{max}$ (CHCl$_3$)=445.5, 619, 669, 677 (sh). For [2·(2H+)·F$^-$]$^+$·PF$_6^-$ (crystals used for X-ray study, $^1$H NMR (CD$_2$Cl$_2$) delta −7.35 (4 H, t, J=41 Hz, NH), −6.20 (1 H, d, J=53 Hz, NH), 2.11–2.36 (18 H m, CH$_2$CH$_3$), 4.31 (6 H, s, CH$_3$), 4.33 (6 H, s, CH$_3$), 4.70–4.82 (12 H, m, CH$_2$CH$_3$), 11.43 (2 H, s, meso-H), 11.49 (2 H, s, meso-H); $^{19}$F NMR (CD$_2$Cl$_2$) delta −73.9 (d, J=750 Hz, PF$_6^-$), −153.7, −153.8 (ca. 1:4 ratio, F$^-$); Laser Desorption MS, 600 ([M+H]$^+$), 620 ([M+H+HF]$^+$); Vis lambda-$_{max}$ (CHCl$_3$)=445.5, 618, 668 677 (sh).

3,12,13,22-Tetraethyl-8,17-di(ethoxycarbonylmethyl)-2,17,18,23-tetramethylsapphyrin (3). This compound was obtained using the general sapphyrin synthesis outlined above. From 4,4'-diethyl-5,5'-diformyl-3,3'-dimethyl-2,2'-bipyrrole(5) (276 mg, 1.00 mmol) and 2,5-bis(5-carboxy-3-ethoxycarbonylmethyl-4-methylpyrrol-2-ylmethyl)-3,4-diethylpyrrole (12) (570 mg, 1.00 mmol) and 740 mg of p-toluene-sulfonic acid monohydrate catalyst were obtained 280 mg (39%) of 3 after chromatography and recrystallization from $CH_2Cl_2$/hexanes. For $[3\cdot(2H+)]^{2+}\cdot[2Cl^-]^{2-}$ $^1H$ NMR (CDCL$_3$) delta $-4.70$ (2 H, s, NH), $-4.48$ (1 H, s, NH), $-4.11$ (2 H, s, NH), 1.40 (6 H, t, J=6.95 Hz, OCH$_2$CH$_3$), 2.19 (6 H, t, J=7.20 Hz, CH$_2$CH$_3$), 2.30 (6 H, t, J=7.06 Hz, CH$_2$CH$_3$), 4.11 (6H, s, CH$_3$), 4.40 (4 H, q, J=7.11 Hz, (OCH$_2$CH$_3$) 4.55 (4 H, q, J=7.22 Hz, CH$_2$CH$_3$), 4.72 (4 H, q, J=7.17 Hz, CH$_2$CH$_3$), 5.65 (4 H, s, CH$_2$CO$_2$Et), 11.72 (2 H, s, meso-H), 11.76 (2 H, s, meso-H), Vis lambda-$_{max}$ (CHCl$_3$)=458.5, 579, 623, 671, 691 nm; For [3] HRMS 715.4099 (calcd for $C_{44}H_{53}N_5O_4$; 715.4098); Vis lambda-$_{max}$=459, 607, 648, 665, 711 nm.

3,12,13,22-Tetraethyl-8,17-di(carboxymethyl)-2,7,18,23-tetramethyl-sapphyrin (4). 3,12,13,22-Tetraethyl-8,17-di(ethoxycarbonylmethyl)-2,7,18,23-tetramethylsapphyrin (3) (20 mg, 0.03 mmol) was dissolved in 30 ml of N$_2$ purged 95% ethanol and then treated with an excess of NaOH dissolved in H$_2$O (15–20 ml). The mixture was stirred and heated at reflux for 12 hours under N$_2$ before the ethanol was removed on the rotary evaporator and the residue taken up in H$_2$O. The pH of the solution was adjusted to 4–5 with 5N HCl, whereupon the product precipitated out and was collected by filtration through a fine glass fritted funnel. Recrystallization from MeOH/H$_2$O gave 15 mg (81%) of (4). Vis (CH$_3$OH) lambda-$_{max}$ (epsilon) 422(sh), 445, 618, 670, 698.

Figure 4:
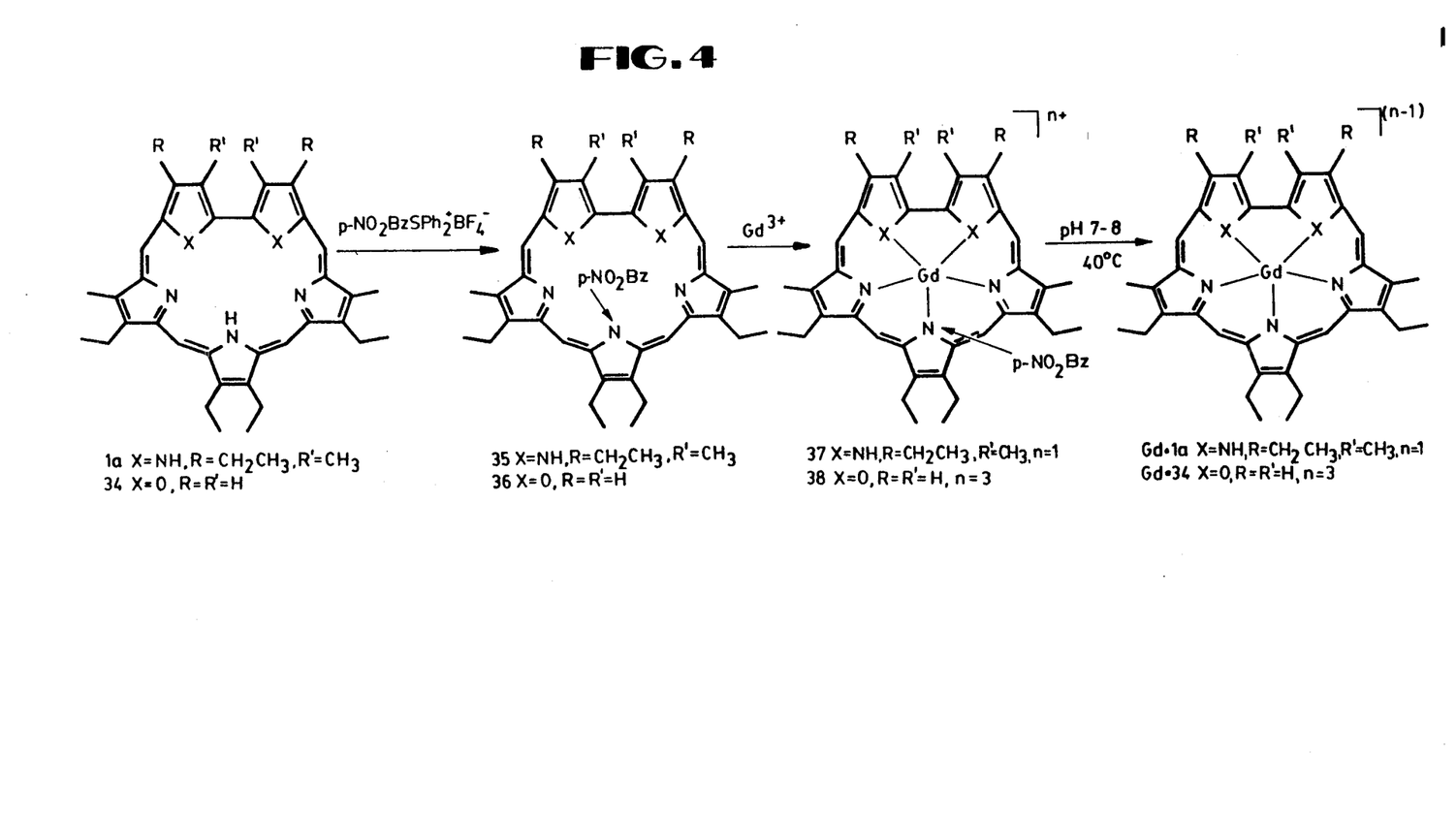
FIG. 4 shows the routine of pentavalent gadolinium complex formation with a dioxysapphyrin.
Figure 5A:
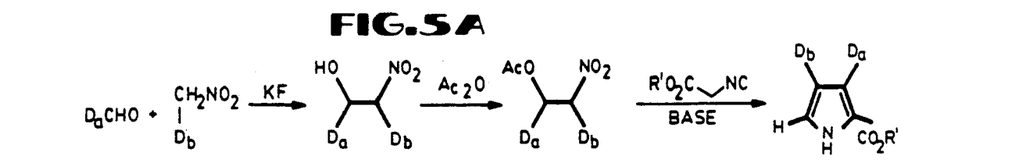
Figure 5B:
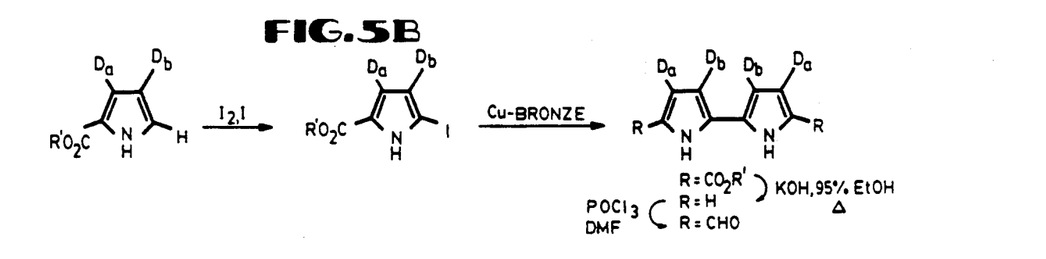
Figure 5C:
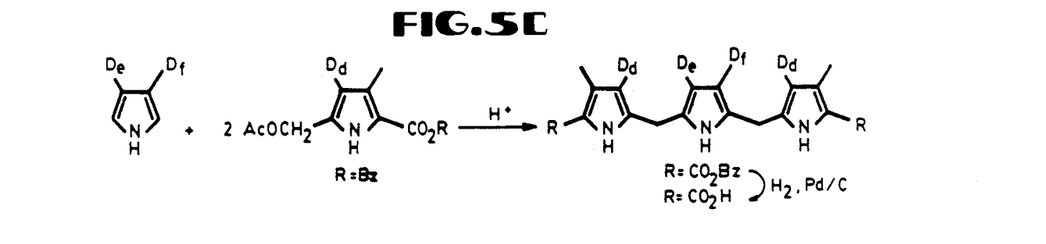
Figure 5D:
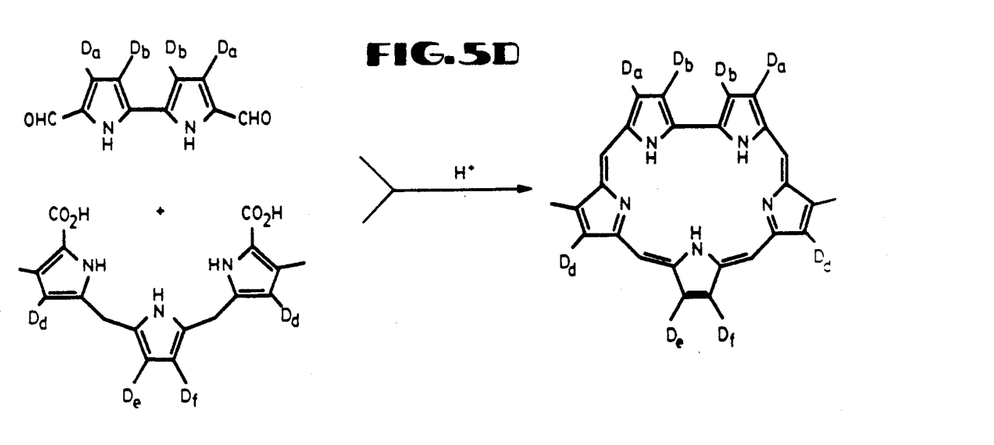

One of the great surprises of sapphyrin chemistry has been the failure of this system to act as a pentadentate ligand. The sapphyrins as a class should be ideal trianionic pentadentate aromatic ligands, perfectly sized for binding, among others, trivalent cations of the lanthanide and actinide series. However, many groups have tried without success to prepare such pentaligated complexes. In particular, over the last nine months the present inventors have tested and found unsuccessful all possible direct metal insertion methods based on or "borrowed" from the known metalloporphyrin literature. These failures led to the consideration that an indirect Lavallee-inspired (Mercer-Smith, J. A.; Roberts, J. C.; Figard, S. D.; Lavallee, D. K. in *Antibody-Mediated Delivery Systems*, Rodwell, J. D. Ed., Marcel Dekker: New York; 1988, pp. 317–352) procedure, such as that shown in FIG. 4, might prove more effective. With the dioxosapphyrin (which is the only compound tried so far), this method of metal complex synthesis appears successful; i.e. results in, or allows the preparation of a pentavalent Gd$^{3+}$ dioxysapphyrin complex.

Literature citations in the above text are incorporated in pertinent part by reference herein for the reasons cited.

It is understood that the steps in the following claims are not in critical order, in that the various precursors being condensed, for example, may be produced in any order of preference. Additionally, those skilled in the art of synthetic organic chemistry would also understand analogous substituents and conditions which could be used within the spirit and scope of the following claims. For example, in place of the various benzyl esters described herein, esters of different structures may be used, e.g. t-butyl groups which may be removed under acidic conditions; ethyl groups which may be removed under saponification conditions, etc. Furthermore, while it is also apparent that the various intermediates and/or reactants may be commercially commissioned and/or obtained to avoid certain claimed steps, such manipulations should not avoid the scope of these claims.

What is claimed is:

1. A method for synthesizing sapphyrins comprising the steps of:
 (A) reacting an alkyl derivative$_a$ aldehyde and an n-nitromethylenealkyl derivative$_b$ to produce beta-hydroxynitroalkyl derivative$_c$;
 (B) reacting the beta-hydroxynitroalkyl derivative$_c$ with acetic anhydride to form beta-acetoxynitroalkyl derivative$_c$;
 (C) reacting the beta-acetoxynitroalkyl derivative$_c$ with ethyl isocyanoacetate in the presence of a nonnucleophilic base to form ethyl 3-alkyl derivative$_a$-4-alkyl derivative$_b$pyrrole-2-carboxylate;
 (D) reacting ethyl 3-alkyl derivative$_a$-4-alkyl derivative$_b$pyrrole-2-carboxylate with iodine and iodide to form ethyl 3-alkyl derivative$_a$-4-alkyl derivative$_b$-5-iodopyrrole-2-carboxylate;
 (E) coupling two molecular equivalents of ethyl 3-alkyl derivative$_a$-4-alkyl derivative$_b$-5-iodo-pyrrole-2-carboxylate in the presence of copper bronze and heat to produce diethyl 4,4'-dialkyl derivative$_a$-3,3'-dialkyl derivative$_b$-2,2'-bipyrrole-5,5'-dicarboxylate;
 (F) converting diethyl 4,4'-dialkyl derivative$_a$-3,3'-dialkyl derivative$_b$-2,2'-bipyrrole-5,5'-dicarboxylate to 4,4'-dialkyl derivative$_a$-3,3'-dialkyl derivative$_b$-2,2'-bipyrrole by saponification and decarboxylation;
 (G) reacting 4,4'-dialkyl derivative$_a$-3,3'-dialkyl derivative$_b$-2,2'-bipyrrole with dimethylformamide and phosphorus oxychloride to form 4,4'-dialkyl derivative$_a$-5,5'-diformyl-3,3'-dialkyl derivative$_b$-2,2'-bipyrrole;
 (H) treating benzyl 4-alkyl derivative$_d$-3,5-dimethylpyrrole-2-carboxylate with an oxidizing agent to produce benzyl 5-(X-methyl)-4-alkyl derivative$_d$-3-methylpyrrole-2-carboxylate;
 (I) condensing two molecular equivalents of benzyl 5-(X-methyl)-4-alkyl derivative$_d$-3-methylpyrrole-2-carboxylate with 3-alkyl derivative$_e$-4-alkyl derivative$_f$pyrrole under acidic conditions to produce 2,5-bis(5-benzyloxycarbonyl-3-alkyl derivative$_d$-4-methylpyrrol-2-ylmethyl)-3-alkyl derivative$_e$-4-alkyl derivative$_f$pyrrole;
 (J) hydrogenating 2,5-bis(5-benzyloxycarbonyl-3-alkyl derivative$_d$-4-methylpyrrol-2-ylmethyl)-3-alkyl derivative$_e$-4-alkyl derivative$_f$pyrrole to produce 2,5-bis(5-carboxy-3-alkyl derivative$_d$-4-methylpyrrol-2-ylmethyl)-3-alkyl derivative$_e$-4-alkyl derivative$_f$pyrrole; and
 (K) condensing 4,4'-dialkyl derivative$_a$-5,5'-diformyl-3,3'-dialkyl derivative$_b$-2,2'-bipyrrole with 2,5-bis(5-carboxy-3-alkyl derivative$_d$-4-methylpyrrol-2-ylmethyl)-3-alkyl derivative$_e$-4-alkyl derivative$_f$pyrrole under acidic oxidizing conditions to produce a 2,23-dialkyl derivative$_b$-3,22-dialkyl derivative$_a$-7,18-dimethyl-8,17-dialkyl derivative$_d$-12-alkyl derivative$_e$-13-alkyl derivative$_f$sapphyrin;

wherein alkyl derivative$_a$, alkyl derivative$_b$, alkyl derivative$_c$, alkyl derivative$_d$, alkyl derivative$_e$ and alkyl derivative$_f$ are independently alkane, functionalized alkane, derivatized alkane or derivatized functional alkane and x is a substituent capable of leaving as an anionically stable moiety.

2. The method of claim 1 wherein the functionalized alkane is an alkane with one or more chemically reactive amino, hydroxyl, carboxyl, carbonyl, cyanate, isocyanate, thiocyanate, sulfhydryl, nitrile, diazo, iodide, disulfide or sulfonic substituents; and when the chemically reactive substituent is isocyanate, thiocyanate, or diazo, said substituent is formed from a carboxyl substituent after step K.

3. The method of claim 1 wherein the derivatized alkane is an alkane with an alkenyl, alkynyl, cycloalkyl or halide (other than iodide) substituent.

4. The method of claim 1 wherein the derivatized functional alkane is an amide, ester, ether or disulfide.

5. A method for producing an alkyl substituted sapphyrin, the method comprising:
   (A) reacting propionaldehyde and nitroethane to produce 4-nitro-3-pentanol;
   (B) reacting 4-nitro-3-pentanol with acetic anhydride to form 3-acetoxy-2-nitropentane;
   (C) reacting 3-acetoxy-2-nitropentane with ethyl isocyanoacetate in the presence of a nonnucleophilic base to form ethyl 3-ethyl-4-methylpyrrole-2-carboxylate;
   (D) reacting ethyl 3-ethyl-4-methylpyrrole-2-carboxylate with iodine and iodide to form ethyl 3-ethyl-5-iodo-4-methylpyrrole-2-carboxylate;
   (E) coupling two molecular equivalents of ethyl 3-ethyl-5-iodo-4-methylpyrrole-2-carboxylate in the presence of copper-bronze and heat to produce diethyl 4,4'-diethyl-3,3'-dimethyl-2,2'-bipyrrole-5,5'-dicarboxylate;
   (F) converting diethyl 4,4'-diethyl-3,3'-dimethyl-2,2'-bipyrrole-5,5'-dicarboxylate to 4,4'-diethyl-3,3'-dimethyl-2,2'-bipyrrole by saponification and decarboxylation;
   (G) reacting 4,4'-diethyl-3,3'-dimethyl-2,2'-bipyrrole with dimethylformamide and phosphorus oxychloride to form 4,4'-diethyl-5,5'-diformyl-3,3'-dimethyl-2,2'-bipyrrole;
   (H) condensing 3,4-diethylpyrrole with two molecular equivalents of benzyl 5-(acetoxymethyl)-4-ethyl-3-methylpyrrole-2-carboxylate to produce 2,5-bis(5-benzyloxycarbonyl-3-ethyl-4-methylpyrrol-2-ylmethyl)-3,4-diethylpyrrole;
   (I) hydrogenating 2,5-bis(5-benzyloxycarbonyl-3-ethyl-4-methylpyrrol-2-ylmethyl)-3,4-diethylpyrrole to produce 2,5-bis(5-carboxy-3-ethyl-4-methylpyrrol-2-ylmethyl)-3,4-diethylpyrrole; and
   (J) condensing 4,4'-diethyl-5,5'-diformyl-3,3'-dimethyl-2,2'-bipyrrole and 2,5-bis(5-carboxy-3-ethyl-4-methylpyrrol-2-ylmethyl)-3,4-diethyl-pyrrole under acidic oxidizing conditions to produce 3,8,12,13,17,22-hexaethyl-2,7,18,23-tetramethylsapphyrin.

6. A method for producing a carboxy substituted sapphyrin, the method comprising:
   (A) reacting propionaldehyde and nitroethane to produce 4-nitro-3-pentanol;
   (B) reacting 4-nitro-3-pentanol with acetic anhydride to form 3-acetoxy-2-nitropentane;
   (C) reacting 3-acetoxy-2-nitropentane with ethyl isocyanoacetate in the presence of a nonnucleophilic base to form ethyl 3-ethyl-4-methylpyrrole-2-carboxylate;
   (D) reacting ethyl 3-ethyl-4-methylpyrrole-2-carboxylate with iodine and iodide to form ethyl 3-ethyl-5-iodo-4-methylpyrrole-2-carboxylate;
   (E) coupling two molecular equivalents of ethyl 3-ethyl-5-iodo-4-methylpyrrole-2-carboxylate in the presence of copper bronze and heat to produce diethyl 4,4'-diethyl-3,3'-dimethyl-2,2'-bipyrrole-5,5'-dicarboxylate;
   (F) converting diethyl 4,4'-diethyl-3,3'-dimethyl-2,2'-bipyrrole-5,5'-dicarboxylate to 4,4'-diethyl-3,3'-dimethyl-2,2'-bipyrrole by saponification and decarboxylation;
   (G) reacting 4,4'-diethyl-3,3'-dimethyl-2,2'-bipyrrole with dimethylformamide and phosphorus oxychloride to form 4,4'-diethyl-5,5'-diformyl-3,3'-dimethyl-2,2'-bipyrrole;
   (H) reacting benzyl 4-ethoxycarboxylmethyl-3,5-dimethylpyrrole-2-carboxylate with lead tetraacetate to produce benzyl 5-(acetoxymethyl)-4-ethoxycarbonylmethyl-3-methylpyrrole-2-carboxylate;
   (I) condensing 3,4-diethylpyrrole with two molecular equivalents of benzyl 5-(acetoxymethyl)-3-ethoxycarbonylmethyl-4-methylpyrrole-2-carboxylate under acidic conditions to produce 2,5-bis(5-benzyloxycarbonyl-3-ethoxycarbonylmethyl-4-methylpyrrol-2-ylmethyl)-3,4-diethylpyrrole;
   (J) hydrogenating 2,5-bis(5-benzyloxycarbonyl-3-ethoxycarbonylmethyl-4-methylpyrrol-2-ylmethyl)-3,4-diethylpyrrole to produce 2,5-bis(5-carboxy-3-ethoxycarbonylmethyl-4-methylpyrrol-2-ylmethyl)-3,4-diethylpyrrole;
   (K)
   (a) condensing 4,4'-diethyl-5,5'-diformyl-3,3'-dimethyl-2,2'-bipyrrole and 2,5-bis(5-carboxy-3-ethoxycarbonylmethyl-4-methylpyrrol-2-ylmethyl)- 3,4-diethylpyrrole under acidic oxidizing conditions to produce 3,12,13,22-tetraethyl-8,17-di(ethoxycarbonylmethyl)-2,7,19,23-tetramethylsapphyrin; and
   (b) producing 3,12,13,22-tetraethyl-8,17-di(ethoxycarbonylmethyl)-2,7,18,23-tetramethylsapphyrin as described in step (K) (a) and saponifying it to produce 3,12,13,22-tetraethyl-8,17-di(carboxymethyl)-2,7,18,23-tetramethylsapphyrin; or
   (c) producing 3,12,13,22-tetraethyl-8,17-di(ethoxycarbonylmethyl)-2,7,18,23-tetramethylsapphyrin as described in step (K) (a) and partially saponifying it to produce 3,12,13,22-tetraethyl-8-(ethoxy-carbonylmethyl)-17-(carboxymethyl)-2,17,18,23-tetramethylsapphyrin.

7. A method for synthesizing dioxosapphyrins comprising the steps of:
   (A) reacting benzyl 4-alkyl derivative$_d$-3,5-dimethylpyrrole-2-carboxylate with an oxidizing agent to produce benzyl 5-(X-methyl)-4-alkyl derivative$_d$-3-methylpyrrole-2-carboxylate;
   (B) condensing two molecular equivalents of benzyl 5-(X-methyl)-4-alkyl derivative$_d$-3-methylpyrrole-2-carboxylates with 3-alkyl derivative$_e$-4-alkyl derivative$_f$pyrrole under acidic conditions to produce 2,5 -bis(5-benzyloxycarbonyl-3-alkyl derivative$_d$-4-methylpyrrol-2-ylmethyl)-3-alkyl derivative$_e$-4-alkyl derivative$_f$pyrrole;
   (C) hydrogenating 2,5-bis(5-benzyloxycarbonyl-3-alkyl derivative$_d$-4-methylpyrrol-2-ylmethyl)-3-alkyl derivative$_e$-4-alkyl derivative$_f$pyrrole to produce 2,5-bis(5-carboxy-3-alkyl derivative$_d$-4-methylpyrrol-2-ylmethyl)-3-alkyl derivative$_e$-4-alkyl derivative$_f$pyrrole; and (D) reacting furfuraldehyde and palladium acetate to produce 5,5'-diformyl-2,2'-bifuran;

(E) condensing 5,5'-diformyl-2,2'-bifuran and 2,5-bis(5-carboxy-3-alkyl derivative$_d$-4-methylpyrrol-2-ylmethyl)-3-alkyl derivative$_e$-4-alkyl derivative$_f$-pyrrole under acidic oxidizing conditions to produce 8,17-dialkyl derivative$_d$-12-alkyl derivative$_e$-13-alkyl derivative$_f$-7,18-dimethyldioxosapphyrin;

wherein alkyl derivative$_d$, alkyl derivative$_e$ and alkyl derivative$_f$ are independently alkane, functionalized alkane, derivatized alkane or derivatized functional alkane and X represents a substituent which may leave as an anionically stable moiety.

8. The method of claim 7 wherein the functionalized alkane is an alkane with one or more chemically reactive amino, hydroxyl, carboxyl, carbonyl, cyanate, isocyanate, thiocyanate, sulfhydryl, nitrile, diazo, iodide, disulfide or sulfonic substituents; and when the chemically reactive substituent is isocyanate, thiocyanate, or diazo, said substituent is formed from a carboxyl substituent after step E.

9. The method of claim 7 wherein the derivatized alkane is an alkane with one or more alkenyl, alkynyl, cycloalkyl or halide (other than iodide) substituents.

10. The method of claim 7 wherein the derivatized functional alkane is one or more of an amide, ester, ether or disulfide substituent.

* * * * *

UNITED STATES PATENT AND TRADEMARK OFFICE
CERTIFICATE OF CORRECTION

PATENT NO.   :   5,302,714

DATED        :   April 12, 1994

INVENTOR(S)  :   Sessler et al.

It is certified that error appears in the above-identified patent and that said Letters Patent is hereby corrected as shown below:

In claim 6, column 18, line 40, delete "19" and insert --18--, therefor.

Signed and Sealed this

Second Day of August, 1994

Attest:

BRUCE LEHMAN

Attesting Officer            Commissioner of Patents and Trademarks